United States Patent
Nguyen et al.

(10) Patent No.: US 6,423,145 B1
(45) Date of Patent: Jul. 23, 2002

(54) DILUTE ACID/METAL SALT HYDROLYSIS OF LIGNOCELLULOSICS

(75) Inventors: Quang A. Nguyen, Golden; Melvin P. Tucker, Lakewood, both of CO (US)

(73) Assignee: Midwest Research Institute, Kansas City, MO (US)

(*) Notice: Subject to any disclaimer, the term of this patent is extended or adjusted under 35 U.S.C. 154(b) by 85 days.

(21) Appl. No.: 09/634,978

(22) Filed: Aug. 9, 2000

(51) Int. Cl.$^7$ ................................................. C18K 1/02
(52) U.S. Cl. .................. 127/37; 106/164.5; 106/164.53
(58) Field of Search .......................... 127/37; 106/164.5, 106/164.53

(56) References Cited

U.S. PATENT DOCUMENTS

| | | | |
|---|---|---|---|
| 3,939,286 A | * 2/1976 | Jelks ........................... | 426/312 |
| 4,461,648 A | * 7/1984 | Foody .......................... | 127/37 |
| 4,520,105 A | 5/1985 | Sinner et al. ................. | 435/163 |
| 4,529,699 A | * 7/1985 | Gerez et al. ................. | 435/165 |
| 5,411,594 A | * 5/1995 | Brelsford ..................... | 127/37 |
| 5,536,325 A | 7/1996 | Brink .......................... | 127/43 |
| 5,879,463 A | 3/1999 | Proenca ....................... | 127/37 |
| 6,022,419 A | 2/2000 | Torget et al. ................. | 127/37 |

* cited by examiner

*Primary Examiner*—David Brunsman
(74) *Attorney, Agent, or Firm*—Paul J. White

(57) ABSTRACT

A modified dilute acid method of hydrolyzing the cellulose and hemicellulose in lignocellulosic material under conditions to obtain higher overall fermentable sugar yields than is obtainable using dilute acid alone, comprising:

impregnating a lignocellulosic feedstock with a mixture of an amount of aqueous solution of a dilute acid catalyst and a metal salt catalyst sufficient to provide higher overall fermentable sugar yields than is obtainable when hydrolyzing with dilute acid alone;

loading the impregnated lignocellulosic feedstock into a reactor and heating for a sufficient period of time to hydrolyze substantially all of the hemicellulose and greater than 45% of the cellulose to water soluble sugars; and recovering the water soluble sugars.

15 Claims, 1 Drawing Sheet

DILUTE ACID/METAL SALT HYDROLYSIS OF LIGNOCELLULOSICS

CONTRACTUAL ORIGIN OF THE INVENTION

The United States Government has rights in this invention pursuant to Contract No. DE-AC36-99GO10337 between the United States Department of Energy and the Midwest Research Institute.

BACKGROUND OF THE INVENTION

1. Field of the Invention

The invention relates to hydrolyzing lignocellulosic materials by subjecting milled lignocellulosic material in a reactor to a catalyst comprised of a dilute solution of a metal salt and a strong acid to lower the activation energy (i.e. temperature) of cellulose hydrolysis compared to that normally required for dilute acid hydrolysis. The lower temperature obtained occasions a reduction in the cost of steam and equipment and enables the hydrolysis of both hemicellulose and cellulose to proceed in a single stage with higher glucose yield from cellulose and less degradation of the hemicellulose sugar. The lower temperature also occasions a higher glucose yield in the second-stage of the two-stage dilute acid hydrolysis process.

Lignocellulose is ubiquitous in all wood species and all agricultural and forestry waste. In addition, municipal waste, which typically contains about half waste paper and yard waste, is a source of lignocellulosic materials. Currently, municipal waste is buried or burned at considerable expense to the disposer or the government organization providing solid waste services.

Lignocellulosic biomass is a complex structure of cellulose fibers wrapped in a lignin and hemicellulose sheath. The ratio of the three components varies depending on the type of biomass. Typical ratios are as follows:

|  | Softwoods | Corn Cobs | RDF* |
| --- | --- | --- | --- |
| Cellulose | 42% | 40% | 52% |
| Hemicellulose | 25% | 36% | 26% |
| Lignin | 28% | 13% | 20% |

*RDF = Refuse Derived Fuel from municipal systems waste

Different woods also have different compositions. Softwoods (gymnosperms) generally have more glucommanan and less glucuronoxylan than hardwoods and grasses (angiosperms).

Cellulose is a polymer of D-glucose with $\beta[1\rightarrow 4]$ linkages between each of the about 500 to 10,000 glucose units. Hemicellulose is a polymer of sugars, primarily D-xylose with other pentoses and some hexoses with $\beta[1\rightarrow 4]$ linkages. Lignin is a complex random polyphenolic polymer. Therefore, lignocellulose represents a very cheap and readily available substrate for the preparation of sugars, which may be used alone or microbially fermented to produce alcohols and other industrial chemicals.

Ethanol, one of the alcohols, which can be produced from lignocellulosic biomass, has a number of industrial and fuel uses. Of particular interest is the use of ethanol as an additive to gasoline to boost octane, reduce pollution and to partially replace gasoline in the mixture. This composition is the well known commercial product called "gasohol". It has been proposed to eliminate gasoline completely from the fuel and to burn ethanol alone. Such a fuel would produce considerably less air pollution by not forming as much carbon monoxide or hydrocarbon emissions. Furthermore, gasoline is produced from crude oil, which fluctuates in price, availability, and is the subject of unpredictable world politics.

It has been estimated that about $1\times10^9$ tons of lignocellulosic wastes are produced every year. This amount exceeds the total amount of crude oil consumed per year. In theory, if properly managed, the lignocellulose produced by the United States is sufficient to produce all of the country's needs for liquid fuel if the cellulose and hemicellulose can be completely converted into ethanol. The amount of energy theoretically obtainable from the combustion of cellulose or the glucose or alcohol derived therefrom is about 7200 BTU per pound or roughly equivalent to 0.35 pounds of gasoline. Hemicellulose has similar value when converted into sugars or ethanol. Consequently, cellulose and hemicellulose represent a readily available potential source for ethanol production. The technology for the production of ethanol from grain and fruit for beverage purposes has been well developed for centuries. However, the costs have been relatively high compared to the cost of gasoline. Accordingly, many methods have been proposed to reduce the cost and increase the efficiency of ethanol production.

Among the techniques proposed for the production of fuel grade ethanol include the hydrolysis of cellulose and hemicellulose to produce sugars which can be fermented to produce ethanol. Cellulose in the form of wood, newsprint and other paper, forest, agricultural, industrial and municipal wastes is quite inexpensive compared to grain, fruit, potatoes or sugarcane which is traditionally used to prepare alcohol beverages.

Hydrolysis of lignocellulosic biomass using an acid catalyst to produce sugars has been known for decades but can be costly and requires special equipment. The hydrolyzed sugars themselves are somewhat labile to the harsh hydrolysis conditions and may be degraded to unwanted or toxic byproducts. If exposed to acid for too long, the glucose derived from cellulose degrades into hydroxymethylfurfural, which can be further degraded into levulinic acid and formic acid. Xylose, a hemicellulose sugar, can be degraded into furfural and further to tars and other degradation products.

In order for acid to completely hydrolyze the cellulose and hemicellulose in a lignocellulosic substrate, degradation of the desirable sugars and formation of the toxic byproducts cannot be avoided due to kinetic constraints. On the other hand, to use conditions sufficiently gentle that significant degradation of sugars will not occur does not result in complete hydrolysis of substrate. Furthermore, the acid is corrosive and requires special handling and equipment. Accordingly, in the last twenty years attention has focused on enzymatic hydrolysis of cellulose with cellulase followed by fermentation of the resulting sugars to produce ethanol which in turn is distilled to purify it sufficiently for fuel uses.

Cellulase is an enzyme complex that includes three different types of enzymes involved in the saccharification of cellulose. The cellulase enzyme complex produced by Trichoderma reesei QM 9414 contains the enzymes named endoglucanase (E.C. 3.2.1.4), cellobiohydrolase (E.C.3.2.1.91) and β-glucosidase (E.C.3.2.1.21). Gum et al, *Biochem.Biophys.Acta*, 446:370–86 (1976). The combined synergistic actions of these three enzymes in the cellulase preparation completely hydrolyses cellulose to D-glucose.

However, cellulase cannot completely degrade the cellulose found in native, unpretreated lignocellulose. It appears that the hemicellulose and lignin interfere with the access of the enzyme complex to the cellulose, probably due to their coating of the cellulose fibers. Furthermore, lignin itself can bind cellulase thereby rendering it inactive or less effective for digesting cellulose. For example, raw ground hardwood is only about 10 to 20% digestible into sugars using a cellulase preparation.

2. Description of the Prior Art

U.S. Pat. No. 4,529,699 disclose a process for obtaining ethanol by continuous acid hydrolysis of cellulosic materials by providing a homogenized slurry of heated (160° to 250° C.) cellulosic material continuously into a reactor, adding concentrated acid to the pressurized and heated cellulosic material to obtain hydrolysis, neutralizing and fermenting the resulting aqueous solution to obtain ethanol, and recovering resulting byproducts of methanol, furfural, acetic acid and lignin.

A process for the production of sugars and optionally cellulose and lignin from lignocellulosic raw materials is disclosed in U.S. Pat. No. 4,520,105. The process entails subjecting vegetable materials to a chemical pretreatment with a mixture of water and lower aliphatic alcohols and/or ketones at 100° to 190° C. for a period of from 4 hours to 2 minutes with control of the breakdown of the hemicellulose components followed by separation of residue and a subsequent chemical treatment with a similar solvent mixture at elevated temperatures for a period of from 6 hours to 2 minutes.

U.S. Pat. No. 5,411,594 disclose a hydrolysis process system for continuous hydrolysis saccharification of lignocellulosics in a two-stage plug-flow-reactor system. The process utilizes dilute-acid hydrolysis and is primarily by reverse inter-stage transfer-flow, opposite to biomass, of second-stage surplus of: process heat; dilute-acid; and ingredient and solution water, all in an alpha cellulose hydrolysate, dilute-acid solution. The primary final product is the combined hydrolysate sugars in a single solution, including pentose, hexose and glucose sugars, which are fermented into ethanol and/or Torula yeast. The secondary final solid product is unhydrolyzed lignin solids.

A method of treating biomass material using a two-stage hydrolysis of lignocellulosic material is disclosed in U.S. Pat. No. 5,536,325. The conditions during the first stage is such as to hydrolyze or depolymerize the hemicellulosic component without substantial degradation of resulting monosaccharides and conditions during the second stage being such as to hydrolyze the cellulose to glucose without substantial degradation of the glucose. Hydrolysis in both stages is accomplished by the use of nitric acid, and the pH, retention time, and temperature in both stages are selected to maximize production of the desired monosaccharide or monosaccharides.

U.S. Pat. No. 6,022,419 disclose a multi-function process for hydrolysis and fractionation of lignocellulosic biomass to separate hemicellulosic sugars from other biomass components such as extractives and proteins; a portion of the solubilized lignin; cellulose; glucose derived from cellulose; and insoluble lignin from the biomass by introducing a dilute acid into a continual shrinking bed reactor containing a lignocellulosic material at 94° to 160° C. for 10 to 120 minutes at a volumetric flow rate of 1 to 5 reactor volumes to solubilize extractives, lignin, and protein by keeping the solid-to-liquid ratio constant throughout the solubilization process.

A process for rapid acid hydrolysis of lignocellulosic material is disclosed in U.S. Pat. No. 5,879,463. The process is a continuous process for acid hydrolysis of lignocellulosic material through which delignification and saccharification are carried out in a single reaction cycle employing a solubilizing organic solvent of lignin and a strong and extremely diluted inorganic acid to obtain highly concentrated recoveries of sugar.

There is a need in the art of obtaining fermentable sugars from lignocellulosic materials under mild conditions to prevent degradation of desirable sugars and formation of toxic byproducts normally obtained from acids used to completely hydrolyze the cellulose and hemicellulose in a lignocellulosic substrate, and yet avoid the incomplete hydrolysis of substrate resulting from sufficiently gentle acid hydrolysis that results in insignificant degradation of the sugars produced.

SUMMARY OF THE INVENTION

One object of the present invention is to provide milder hydrolysis conditions for lignocellulosic materials to reduce the cost of steam and equipment, limit degradation of desirable sugars and the formation of toxic byproducts due to kinetic constraints and to provide more complete hydrolysis of the lignocellulosic substrate.

Another object of the present invention is to provide milder hydrolysis conditions for lignocellulosic materials to reduce the cost of steam and equipment and limit degradation of desirable sugars and the formation of toxic byproducts, while providing more complete hydrolysis of lignocellulosic substrate, by employing a combination of a dilute acid catalyst and a metal salt catalyst.

A further object of the present invention is to provide milder hydrolysis conditions for lignocellulosic materials to reduce the cost of steam and equipment and limit degradation of desirable sugars and the formation of toxic byproducts, while providing more complete hydrolysis of lignocellulosic substrate, by employing a combination of a dilute acid catalyst and a metal salt catalyst to achieve both hemicellulose and cellulose hydrolysis in a single stage.

A yet further objective of the invention is to achieve a higher glucose yield in a two-stage dilute acid hydrolysis process.

In general, the lignocellulosic materials of the invention are hydrolyzed by subjecting the milled lignocellulosic material in a reactor to a catalyst comprised of a dilute solution of a metal salt and a strong acid to lower the activation energy (i.e. temperature) of cellulose hydrolysis compared to that normally required for dilute acid hydrolysis. The lower temperature obtained occasions a reduction in the cost of steam and equipment and enables the hydrolysis of both hemicellulose and cellulose to proceed in a single stage with higher glucose yield from cellulose and less degradation of the hemicellulose sugar. The lower temperature also occasions a higher glucose yield in the second-stage of a two-stage dilute acid hydrolysis process.

DETAILED DESCRIPTION OF THE INVENTION

Figure 1:
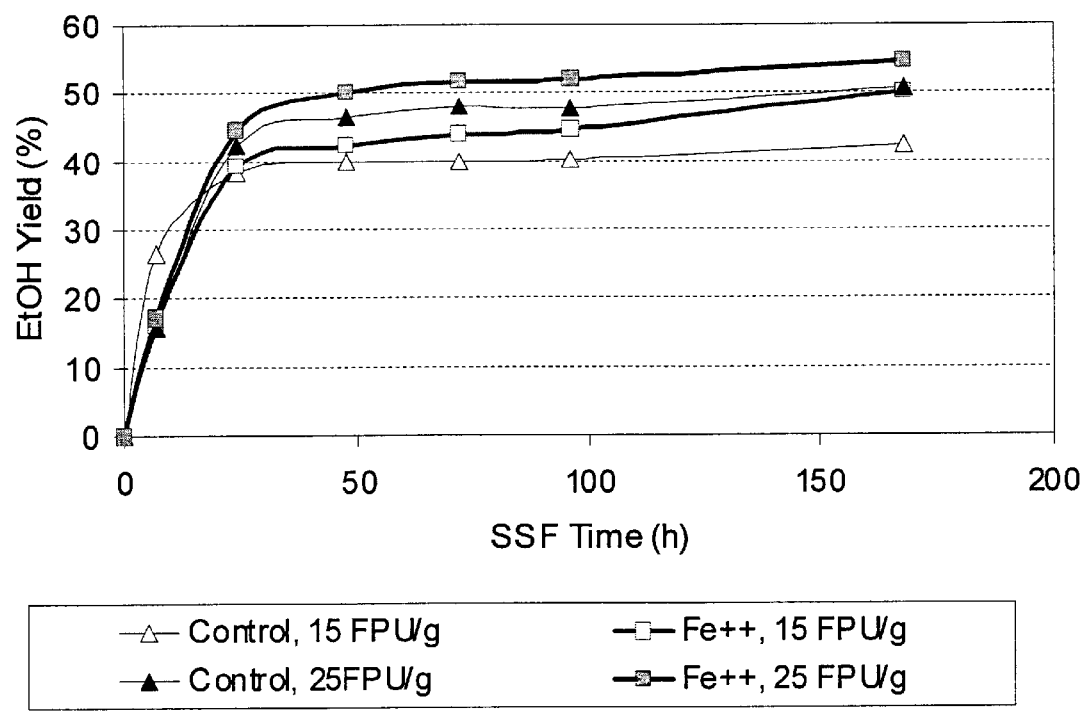
FIG. 1 is a graph showing simultaneous enzymatic saccharification and ethanol fermentation (SSF) of second-stage dilute-acid hydrolyzed whole tree softwood forest thinnings.

The process of the invention is superior to the traditional dilute acid hydrolysis processes of producing sugars in that it hydrolyzes both hemicellulose and cellulose under mild conditions.

Further, in conventional dilute acid hydrolysis of lignocellulosic material, in order to obtain high yields of sugar from both hemicellulose and cellulose, the hydrolysis is normally done in two stages since the more severe conditions (high temperature or high acid concentration) required for hydrolysis of the cellulose causes degradation of the hemicellulosic sugar.

The invention process utilizes lignocellulosic materials (such as softwood, hardwood, agricultural residues, corn refining residues, grasses, etc.) by first milling these materials and then impregnating these milled materials with an aqueous solution of acid ($H_2SO_4$, HCl, $HNO_3$ and $SO_2$ or any other strong acid which effect pH values below about pH 3) and a metal salt (ferrous sulfate, ferric sulfate, ferric chloride, aluminum sulfate, aluminum chloride, and magnesium sulfate) in an amount sufficient to provide higher overall fermentable sugar yields than is obtainable when hydrolyzing with dilute acid alone.

Sulfuric acid is preferred, and when sulfuric acid is used as the dilute acid catalyst, it is used in a concentration range of from about 0.2 to about 4% by weight, along with the preferred metal salt catalyst of ferrous sulfate in a concentration range of from about 0.2 to about 25.0 mmole/L. After the lignocellulosic material is impregnated with this combination of dilute acid catalyst and metal salt catalyst and excess liquid is drained from the material, the impregnated lignocellulosic material is heated to a range of from about 120° to 240° C. for a period of about 1 to about 30 minutes to hydrolyze the hemicellulose and cellulose fractions to sugars. The mixture is then cooled to less than about 105° C. to minimize degradation of the sugars. A batch steam explosion reactor or a continuous reactor may be used to implement the hydrolysis process.

When the process utilizes a batch or continuous steam explosion reactor, the catalyst-impregnated feedstock is loaded into the steam explosion reactor and heated with steam at 120° C.–240° C. for 1–30 minutes to hydrolyze essentially all the hemicellulose and greater than 45% of the cellulose to water soluble sugars (monomers and oligomers).

The contents of the reactor are then discharged into a flask tank where condensate is flashed off. The sugars can then be recovered from the solids using a counter-current washing device. The remaining cellulose in the solids can be readily hydrolyzed to glucose with cellulase enzymes.

Another application of dilute acid and metal salt catalyzed hydrolysis of lignocellulosic materials is in two-stage hydrolysis process. In the first-stage hydrolysis, essentially all the hemicellulose can be hydrolyzed using dilute acid or dilute acid and metal salt catalysts. The soluble sugars are removed from the first-stage hydrolysate using a counter-current washing device. The remaining cellulose can be partially hydrolyzed to glucose in the second-stage using dilute acid and metal salt catalyzed hydrolysis. The residual cellulose after the second-stage hydrolysis can be further hydrolyzed to glucose with cellulase enzymes.

EXAMPLE I

Application of ferrous sulfate ($FeSO_4 \cdot 7H_2O$) in single-stage dilute sulfuric acid hydrolysis of Douglas fir wood chips.

Douglas fir chips (obtained from debarked logs) were soaked in three separate solutions of (i) 0.35% (w/w) sulfuric acid, (ii) 0.35% sulfuric acid and 0.5 mmole ferrous sulfate/L, and (iii) 0.35% sulfuric acid and 2 mmole ferrous sulfate/L. The temperature of the acid solutions was maintained at 60° C. and the soaking time was 6 hr. Excess liquid was drained from the three batches of wood chips, which were then hydrolyzed separately at 214° C. for 100 s in a 4-L steam explosion reactor. Hydrolysis treatment of the first feedstock (non-ferrous sulfate) was done in ten replicates and the resulting hydrolyzed materials were blended together to make one sample. The feedstocks impregnated with dilute sulfuric acid and ferrous sulfate were each hydrolyzed in duplicate batches. The composition of Douglas Fir feedstocks and insoluble solids obtained from hydrolyzed Douglas Fir Chips are shown in TABLE 1.

The compositions of the hydrolysate liquors (obtained by pressing the hydrolyzed chips) are shown in TABLE 2.

TABLE 3 summarizes the soluble sugar recovery yields in the hydrolysate liquors.

TABLE 1

Composition (in weight %) of Douglas fir (DF) feedstocks and insoluble solids obtained from hydrolyzed DF chips

| Sample | GLU | XYL | GAL | ARA | MAN | LIG | ASH |
| --- | --- | --- | --- | --- | --- | --- | --- |
| Acid-impregnated DF chips (no ferrous sulfate) | 44.08 | 5.97 | 3.74 | 2.96 | 13.24 | 30.17 | 0.14 |
| Acid-impregnated DF chips (0.5 mmole ferrous sulfate/L) | 44.31 | 6.46 | 4.06 | 2.57 | 14.11 | 29.67 | 0.14 |
| Acid-impregnated chips (2 mmole ferrous sulfate/L) | 43.85 | 6.41 | 3.91 | 2.55 | 13.73 | 30.20 | 0.15 |
| DF970102-01 (no ferrous sulfate) hydrolyzed @ 214° C. & 100s | 51.21 | 0.04 | 0.10 | 0.04 | 0.74 | 45.43 | 0.08 |
| DF970102-02 (0.5 mmole ferrous sulfate/L) | 36.65 | 0.03 | 0.17 | 0.03 | 0.79 | 60.88 | 0.11 |

TABLE 1-continued

Composition (in weight %) of Douglas fir (DF) feedstocks and insoluble solids obtained from hydrolyzed DF chips

| Sample | GLU | XYL | GAL | ARA | MAN | LIG | ASH |
|---|---|---|---|---|---|---|---|
| hydrolyzed @ 214° C. & 100s | | | | | | | |
| DF97012-03 (2 mmole ferrous sulfate/L) hydrolyzed @ 214° C. & 100s | 40.47 | 0.05 | 0.16 | 0.03 | 0.84 | 58.88 | 0.05 |

GLU = glucose;
XYL = xylose;
GAL = galactose;
ARA = arabinose;
MAN = mannose;
LIG = lignin (Klason acid-insoluble lignin + acid-soluble lignin);
ASH = total ash.

TABLE 2

Composition of hydrolysate liquors (in g/L).
(Note: values in parentheses are sugar concentrations after 4% sulfuric acid post hydrolysis at 121° C. for 1 hr)

| Hydrolysate liquor sample | GLU | XYL | GAL | ARA | MAN |
|---|---|---|---|---|---|
| DF970102-01 (no ferrous sulfate) | 46.89 (55.1) | 16.21 (16.48) | 12.01 (13.62) | 5.78 (6.15) | 27.54 (33.49) |
| DF970102-02 (0.5 mmole ferrous sulfate/L) | 88.11 (105.98) | 10.69 (11.97) | 12.02 (12.66) | 4.96 (5.28) | 21.96 (28.81) |
| DF970102-03 (2 mmole ferrous sulfate/L) | 87.68 (99.14) | 12.68 (12.66) | 13.07 (12.77) | 5.92 (5.38) | 24.3 (29.58) |

GLU = glucose;
XYL = xylose;
GAL = galactose;
ARA = arabinose;
MAN = mannose

TABLE 3

Soluble sugar recovery yield from dilute-acid hydrolysis of Douglas fir

| Sample | Glucose (g/100 g dry wood) | Total sugar* (g/100 g dry wood) |
|---|---|---|
| DF970102-01 (no ferrous sulfate) | 12.2 (control) | 27.8 (control) |
| DF970102-02 (0.5 mmole ferrous sulfate/L) | 23.8 (95% increase over control) | 37.0 (33% increase over control) |
| DF970102-03 (2 mmole ferrous sulfate/L) | 23.0 (89% increase over control) | 37.0 (33% increase over control) |

*Total sugar includes glucose, xylose, galactose, arabinose and mannose.

The results show that under the same hydrolysis conditions (i.e., same hydrolysis temperature, time and sulfuric acid concentrations), the addition of a small amount of ferrous sulfate significantly increases the glucose yield from cellulose. Sample DF970102-01 was produced using standard acid hydrolysis with no ferrous sulfate added, samples DF970102-02 and DF970102-03 with ferrous sulfate added at 0.5 mmole/L and 2 mmole/L respectively.

Based on the composition of washed samples (TABLE 1), all the hemicellulose (xylan, galactan and mannan) were essentially solubilized in all hydrolyzed materials. Sample 01 (no ferrous sulfate added) contains 51.2% glucose, whereas in samples 02 (0.5 mmole ferrous sulfate/L) and 03 (2 mmole ferrous sulfate/L) the glucose content was reduced to 36.6% and 40.5% respectively.

The higher extent of hydrolysis of cellulose in samples 02 and 03 result in higher glucose concentration in the hydrolysate. TABLE 2 shows the glucose concentrations (after post hydrolysis of the hydrolysate liquor with 4% sulfuric acid) of 55.1 g/L in sample 01, 106 g/L in sample 02, and 99.1 g/L in sample 03. The hemicellulose sugar concentrations of the last two samples are slightly lower than those of sample 01. The results clearly indicate that the addition of ferrous sulfate improved the total sugar yield significantly (about 33%).

TABLE 4 shows the estimated glucan conversions (calculated from the glucan contents of the residual solids) of hydrolyzed Douglas Fir: Basis: 100 g feedstock (dry weight); Hydrolyzed material=90 g (dry weight), 10 g loss (volatile components); and Water insoluble (WI)= Hydrolyzed material*(1−water-soluble fraction).

It is apparent that the addition of 0.5–2 mmole/L of ferrous sulfate in the impregnation stage improves the overall sugar yield from single-stage dilute sulfuric acid hydrolysis of softwood by about 20–30%.

TABLE 4

Dilute acid hydrolysis of Douglas fir with and without ferrous sulfate

| Sample | Water soluble fraction | Water insoluble (WI) (g) | Glucose content in WI (%) | Glucose content in WI (g) | Glucan hydrolyzed (% theoretical) |
|---|---|---|---|---|---|
| Feedstock | N/A | 100 g | 44.0 | 44.0 | N/A |
| #001 (no ferrous sulfate) | 0.307 | 62.3 | 51.2 | 31.9 | 27.5 |
| #002 (0.5 mmole ferrous sulfate/L) | 0.327 | 60.6 | 36.6 | 22.2 | 49.5 |
| #003 (2 mmole ferrous sulfate/L) | 0.341 | 59.3 | 40.5 | 24.0 | 45.0 |

EXAMPLE II

Application of ferrous sulfate ($FeSO_4.7H_2O$) in single-stage dilute sulfuric acid hydrolysis of mixed softwood chips.

Wood chips (obtained from debranched trees, i.e., including bark but no needles), comprising of approximately 70% White fir and 30% Ponderosa pine, were soaked in two separate solutions of (i) 0.7% (w/w) sulfuric acid, (ii) 0.7% sulfuric acid, and 0.5 mmole ferrous sulfate/L. The temperature of the acid solutions was maintained at 60° C. and the soaking time was 4 hr. Excess liquid was drained from the wood chips. The wood chips soaked with acid but without ferrous sulfate were hydrolyzed at two conditions (i) 210° C. for 2 minutes and (ii) 210° C. for 3 minutes in a 4-L steam explosion reactor. The wood chips soaked with acid and 0.5 mmole ferrous sulfate/L were hydrolyzed at 210° C. for 2 minutes. TABLE 5 summarizes the soluble sugar recovery yields in the hydrolysate liquors.

TABLE 5

Soluble sugar recovery yield from dilute-acid hydrolyzed debranched softwoods (DB-SW) (70% White fir + 30% Ponderosa pine)

| Sample | Glucose (g/100 g dry wood) | Total sugar* (g/100 g dry wood) |
|---|---|---|
| DB-SW970624-02 (no ferrous sulfate) hydrolyzed @ 210° C. & 2 min | 12.1 (control) | 19.4 (control) |
| DB-SW970624-03 (no ferrous sulfate) hydrolyzed @ 210° C. & 3 min | 13.8 (14% increase over control) | 19.4 (no increase over control) |
| DB-SW970707-01 (5 mmole ferrous sulfate/L) hydrolyzed @ 210° C. & 2 min | 15.2 (26% increase over control) | 23.8 (23% increase over control) |

*Total sugar includes glucose, xylose, galactose, arabinose and mannose

Without ferrous sulfate, increasing the hydrolysis time from 2 min to 3 min increased the glucose yield by 14%. The total sugar yield, however, remained the same because at longer hydrolysis time the hemicellulose sugar yield decreased as a result of degradation of the hydrolyzed sugars. When ferrous sulfate was added and hydrolysis was carried out at 210° C. for 2 min, soluble glucose yield increased by 26% over the control sample, and little hemicellulose degradation took place. As a result, the total sugar yield increased by 23%. The increase in total sugar yield for mixed softwoods (debranched White fir and Ponderosa pine) was less than that observed for Douglas fir chips. One possible cause of the lower impact by ferrous sulfate is the higher extractive content of mixed softwoods. The extractive content was 4.4% for Douglas fir chips and 6.2% for mixed softwoods. The high extractive content of the mixed softwoods most likely formed complexes with ferrous sulfate and reduced its effectiveness as a catalyst in dilute acid hydrolysis of lignocellulosic biomass.

EXAMPLE III

Application of ferrous sulfate ($FeSO_4 \cdot 7H_2O$) in the second stage of two-stage dilute sulfuric acid hydrolysis of softwood forest thinnings.

Wood chips obtained from whole tree mixed softwood forest thinnings (i.e. bark and needles included) consisting of approximately 70% White fir and 30% Ponderosa pine were soaked in 2.5% (w/w) sulfuric acid solution at 60° C. for 4 hr. Excess liquid was drained from the wood chips, which were then hydrolyzed at 180° C. for 4 minutes in a 4-L steam explosion reactor. The hydrolyzed materials were washed with water to remove soluble sugars. The washed solids were divided into two equal portions then soaked in separate solutions of (i) 2.5% (w/w) sulfuric acid and (ii) 2.5% (w/w) sulfuric acid and 5 mmole ferrous sulfate/L. Excess liquid was drained from the two batches of materials, which were then hydrolyzed separately at 210° C. for 120 s in a 4-L steam explosion reactor. Essentially all the hemicellulose was removed after first-stage hydrolysis. TABLE 6 summarizes the soluble glucose recovery yields in the hydrolysate liquors and the glucose content of the insoluble solids of starting material and hydrolyzed materials.

TABLE 6

Soluble sugar recovery yield from second-stage dilute-acid hydrolysis of whole tree softwood forest thinnings (WT-SW) (70% White fir + 30% Ponderosa pine).

| Sample | Glucose (g/100 g dry input material*) | Glucose content in washed hydrolyzed material (wt %) |
|---|---|---|
| WT-SW980916-01 (no ferrous sulfate) hydrolyzed @ 210° C. and 2 min | 21.0 (control) | 22.8 |
| WT-SW980916-02 (5 mmole ferrous sulfate/L) hydrolyzed @ 210° C. and 2 min | 22.2 (6% increase over control) | 19.8 |

*Input material is washed-solids from first-stage hydrolysate of whole tree forest thinnings The effectiveness of ferrous sulfate in improving acid hydrolysis of cellulose appears to be significantly reduced by the high content of extractives in bark and needles. The extractive content of whole tree forest thinnings was 7.5% of dry wood (which is significantly higher than 4.4% for Douglas fir chips). Additionally, with approximately 21% of the cellulose solubilized in the first-stage hydrolysis the remaining cellulose is probably more resistant to dilute acid hydrolysis.

Addition of ferrous sulfate in the dilute-acid hydrolysis step also improved the simultaneous saccharification and fermentation (SSF) ethanol yield at low enzyme loading (15–25 FPU/g cellulose) by about 10% as shown in FIG. 1.

FIG. 1. Simultaneous enzymatic saccharification and ethanol fermentation (SSF) of second-stage dilute-acid hydrolyzed whole tree softwood forest thinnings.

Further, the addition of ferrous sulfate reduces the overall enzyme requirement for cellulose hydrolysis because of lower residual cellulose content after the acid hydrolysis and the lower enzyme loading requirements.

Nevertheless, at 0.5 mmole/L ferrous sulfate loading, the cost of the catalyst in single-stage dilute acid hydrolysis is about 3 cents per dry ton of wood input. Therefore, it is apparent that it is cost effective to use ferrous sulfate to improve overall sugar yield.

We claim:

1. A modified dilute acid method of hydrolyzing the cellulose and hemicellulose in lignocellulosic material under conditions to obtain higher overall fermentable sugar yields than is obtainable using dilute acid alone, comprising:

impregnating a lignocellulosic feedstock with a mixture of an amount of aqueous solution of a dilute acid catalyst and a metallic salt catalyst sufficient to hydrolyze the hemicellulose and cellulose fractions to provide higher overall fermentable sugar yields than is obtainable when hydrolyzing with dilute acid alone;

loading said impregnated lignocellulosic feedstock into a reactor and heating for a sufficient period of time to hydrolyze substantially all of the hemicellulose and greater than 45% of the cellulose to water soluble sugars; and recovering said water soluble sugars.

2. The process of claim 1 wherein said reactor is a batch steam explosion reactor.

3. The process of claim 1 wherein said reactor is a continuous reactor.

4. The process of claim 1 wherein said lignocellulosic feedstock is selected from the group consisting of softwood, hardwood, agricultural residues, corn refining residues and grasses.

5. The process of claim 4 wherein said softwood is Douglas Fir, White fir and Ponderosa pine.

6. The process of claim 1 wherein said dilute acid catalyst is selected from the group consisting of $H_2SO_4$, HCl, $HNO_3$, $SO_2$ or any strong acid which effect pH values below about 3, and said metal salt catalyst is selected from the group consisting of ferrous sulfate, ferric sulfate, ferric chloride, aluminum sulfate, aluminum chloride, and magnesium sulfate.

7. The process of claim 6 wherein said amount of aqueous mixture of catalysts sufficient to provide higher overall fermentable sugar yields than is obtainable when hydrolyzing with dilute acid alone is between about 0.2–4.0 weight percent range and between about 0.2 to about 25.0 mmole/L for said metal salt catalyst.

8. The process of claim 7 wherein said dilute acid catalyst is $H_2SO_4$ and said metal salt is ferrous sulfate.

9. The process of claim 8 wherein said heating of the lignocellulosic material for a sufficient period of time is at a temperature of between about 120° C. to about 240° C. for about 1 to about 30 minutes.

10. The process of claim 9 wherein, subsequent to said heating step and prior to recovering water soluble sugars, the mixture is cooled to less than about 105° C. to minimize degradation of sugars.

11. The process of claim 1 wherein said lignocellulosic feedstock is milled prior to impregnation.

12. The process of claim 11 wherein said hydrolysis is conducted in a single stage.

13. The process of claim 11 wherein the hydrolysis is conducted in two stages with an inter-stage washing step to recover soluble sugars from first-stage hydrolysate.

14. A combination of a dilute acid catalyst and a metal salt catalyst at a sufficient temperature to hydrolyze greater than 45% cellulose and substantially all of the hemicellulose in a lignocellulosic material in a single stage to obtain higher overall fermentable sugar yields than is obtainable using dilute acid alone.

15. The combination of claim 14 wherein said dilute acid catalyst is present in a concentration range of from about 0.2 to about 4% by weight and said metal salt catalyst is present in a concentration range of from about 0.2 to about 25 mmole/L.

* * * * *